(12) United States Patent
Kloog et al.

(10) Patent No.: US 8,278,349 B2
(45) Date of Patent: Oct. 2, 2012

(54) CANCER TREATMENT USING FTS AND 2-DEOXYGLUCOSE

(75) Inventors: Yoel Kloog, Herzliya (IL); Liat Goldberg, Ramat Gan (IL); Michael Brownstein, Rockville, MD (US)

(73) Assignee: Ramot at Tel-Aviv University Ltd. (IL)

( * ) Notice: Subject to any disclaimer, the term of this patent is extended or adjusted under 35 U.S.C. 154(b) by 705 days.

(21) Appl. No.: 12/085,628

(22) PCT Filed: Nov. 6, 2006

(86) PCT No.: PCT/US2006/043325
§ 371 (c)(1),
(2), (4) Date: May 27, 2009

(87) PCT Pub. No.: WO2007/064448
PCT Pub. Date: Jun. 7, 2007

(65) Prior Publication Data
US 2009/0286870 A1   Nov. 19, 2009

Related U.S. Application Data

(60) Provisional application No. 60/740,096, filed on Nov. 28, 2005.

(51) Int. Cl.
*A01N 43/16* (2006.01)
*A01N 31/00* (2006.01)
*A61K 31/35* (2006.01)
*A61K 31/10* (2006.01)
*C07D 315/00* (2006.01)
*C07C 319/00* (2006.01)
*C07C 321/00* (2006.01)
*C07C 323/00* (2006.01)
*C07C 381/00* (2006.01)

(52) U.S. Cl. ........ 514/460; 514/712; 514/713; 549/417; 568/38

(58) Field of Classification Search .................. 514/460, 514/712, 713; 549/417; 568/38
See application file for complete search history.

(56) References Cited

U.S. PATENT DOCUMENTS

| 5,705,528 | A  | 1/1998  | Kloog          |
|-----------|----|---------|----------------|
| 6,462,086 | B1 | 10/2002 | Kloog et al.   |
| 6,670,330 | B1 | 12/2003 | Lampidis et al.|
| 2005/0245462 | A1 | 11/2005 | Tidmarsh     |
| 2009/0226512 | A1 | 9/2009  | Bauer         |

FOREIGN PATENT DOCUMENTS

| WO | WO-95/13059 A    | 5/1995  |
| WO | WO-01/82926 A1   | 11/2001 |
| WO | WO-2004/062604 A2| 7/2004  |
| WO | 2006023639 A1    | 3/2006  |
| WO | 2007/064448      | 6/2007  |
| WO | 2007091241 A1    | 8/2007  |
| WO | 2007116396 A1    | 10/2007 |
| WO | 2008075342 A1    | 6/2008  |

OTHER PUBLICATIONS

Gana-Weisz et al, The Ras Inhibitor S-trans, trans—Farnesylthiosalicylic Acid Chemosensitizes Human Tumor Cell Without Causing Resistance[1], Clinical Cancer Research, The American Association for Cancer Research, US, vol. 8, No. 2, pp. 555-565, 2002.
Blum, Roy et al., "Ras Inhibition in Glioblastoma Down-regulates Hypoxia-Inducible Factor-1∝, Causing Glycolysis Shutdown and Cell Death", Cancer Research, vol. 65, No. 3, pp. 999-1006, Feb. 1, 2005.
Downward J, Nat. Rev. Cancer 3:11-22 (2003).
Shields, J. M., et al, Trends Cell Biol 10: 147-541 (2000).
Mitin, N., et al., Curr Biol 15: R563-74 (2005).
Haklai, et al., Biochemistry 37 (5): 1306-14 (1998).
Yaari, S., Jacob-Hirsch, J., Amariglio, N., Haklai, R., Rechavi, G. and Kloog, Y., Clin Cancer Res 11: 4321-30 (2005).
Kloog, Y. and Cox, A.D., Mol. Med. Today 6 : 398-402 (2000).
Dwarakanath, B. S., Khaitan, D. and Ravindranath, T., Cancer Biol. Ther. 3 : 864-70 (2004).
Maher, J. C., Krishan, A. and Lampidis, T. J. Cancer Chemother Pharmacol 53: 116-22 (2004).

*Primary Examiner* — Shengjun Wang
*Assistant Examiner* — Sarah Pihonak
(74) *Attorney, Agent, or Firm* — Lerner, David, Littenberg, Krumholz & Mentlik, LLP (57) ABSTRACT

Methods of treating cancer by administering effective amounts of a Ras antagonist comprising FTS, or analogs thereof, or a pharmaceutically acceptable salt, and 2-deoxyglucose (2DG) to a patient are disclosed. Pharmaceutical compositions useful in treating cancer containing a Ras antagonist comprising FTS, or analogs thereof, or a pharmaceutically acceptable salt, and 2DG are also disclosed.

18 Claims, 12 Drawing Sheets

FIG. 12

CANCER TREATMENT USING FTS AND 2-DEOXYGLUCOSE

CROSS-REFERENCE TO RELATED APPLICATIONS

The present application is a national phase entry under 35 U.S.C. §371 of International Application No. PCT/US2006/043325, filed Nov. 6, 2006, published in English, which claims the benefit of U.S. Provisional Patent Application No. 60/740,096, filed Nov. 28, 2005. The disclosures of all of said applications are incorporated by reference herein.

BACKGROUND OF THE INVENTION

The active Ras protein promotes oncogenesis through activation of multiple Ras effectors that contribute to deregulated cell growth, differentiation, and increased survival, migration and invasion. See e.g., Downward, J., Nat. Rev. Cancer 3:11-22 (2003); Shields, J. M., et al., Trends Cell Biol 10:147-541 (2000); and Mitin, N., et al., Curr. Biol. 15:R563-74 (2005). U.S. Pat. No. 5,705,528 discloses farnesylthiosalicylic acid (FTS) and analogs thereof and their utility as anti-cancer agents. FTS is believed to exert its antagonistic effect by dislodging activated Ras from its membrane anchor protein, thus deactivating activated Ras. See Haklai, et al., Biochemistry 37(5):1306-14 (1998).

SUMMARY OF THE INVENTION

A first aspect of the present invention is directed to a method of treating cancer. The method comprises administering to a patient in need thereof effective amounts of a Ras antagonist comprising farnesylthiosalicylic acid (FTS) or an analog thereof or a pharmaceutically acceptable salt thereof, and 2-deoxyglucose (2DG).

Another aspect of the present invention is directed to a pharmaceutical composition useful in the treatment of cancer. The composition comprises effective amounts of FTS or an analog thereof or a pharmaceutically acceptable salt thereof, 2DG and a carrier. The composition may be present in a form suitable for oral administration, such as a tablet, capsule, which may be a hard or soft gelatin capsule, a powder, a granule, or a solution or a suspension. Methods of making the compositions are further provided.

DETAILED DESCRIPTION

Ras antagonists useful in the present invention are represented by formula I:

wherein
$R^1$ represents farnesyl, geranyl or geranyl-geranyl;
$R^2$ is $COOR^7$, or $CONR^7R^8$, wherein $R^7$ and $R^8$ are each independently hydrogen, alkyl or alkenyl;
$R^3$, $R^4$, $R^5$ and $R^6$ are each independently hydrogen, alkyl, alkenyl, alkoxy, halo, trifluoromethyl, trifluoromethoxy or alkylmercapto; and
X represents S.

These compounds represent farnesyl-thiosalicylic acid (FTS) (i.e., S-trans,trans-FTS, S-cis,trans-FTS) and its analogs. The structure of FTS is as follows:
FTS:

FTS analogs embraced by formula I include 5-fluoro-FTS, 5-chloro-FTS, 4-chloro-FTS, S-farnesyl-thiosalicylic acid methyl ester (FTSME), and S-geranyl geranyl-thiosalicylic acid (GGTS). Structures of these compounds are set forth below.

5-Cl-FTS

4-Cl-FTS

5-F-FTS

FTSME

GGTS

Pharmaceutically acceptable salts of the Ras antagonists of formula I may be useful. These salts include, for example, sodium and potassium salts. In preferred embodiments, however, the Ras antagonist is not in the form of a salt (i.e., non-salified).

Methods for preparing the compounds of formula I are disclosed in U.S. Pat. Nos. 5,705,528 and 6,462,086. Those disclosures (e.g., Example 7 in the '086 patent) are incorporated herein by reference.

2-deoxyglucose (2DG) is an inhibitor of glycolysis. 2-DG has been reported to inhibit glycolysis in cancer cells and thus inhibit their growth. See, U.S. Patent Application 2005/0245462 (and references cited therein). Methods of preparing and using 2DG as an anti-cancer agent are described in, for example, U.S. Pat. No. 6,670,330 and U.S. Patent Application 2005/0245462. Preferably, the 2DG compound is 2-deoxy-D-glucose. The structure of 2-deoxy-D-glucose is as follows:

Cancer generally refers to a disease caused by the uncontrolled, abnormal growth of cells that can spread to adjoining tissues or other parts of the body. Cancer cells can form a solid tumor, in which the cancer cells are massed together, or they can exist as dispersed cells, as in leukemia. Normal cells divide (reproduce) until maturation is attained and then only as necessary for replacement of damaged or dead cells. Cancer cells are often referred to as "malignant", because they divide endlessly, eventually crowding out nearby cells and spreading to other parts of the body. Malignant cancer cells eventually metastasize and spread to other parts of the body via the bloodstream or lymphatic system, where they can multiply and form new tumors. As used herein, "treating" cancer (or treating a patient with cancer) refers to taking steps to obtain beneficial or desired results such as amelioration of symptom(s) of the cancer, diminishment of extent of disease, delay or slowing of disease progression, partial or complete remission and prolonged survival.

Malignant tumors are divided into carcinomas (which arise from epithelial precursor cells), sarcomas (which arise largely from mesenchymal tissues) and lymphomas (which arise from precursors of red and white blood cells). The cancers treatable in accordance with the present invention include but are not limited to human lymphomas, sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, synovioma, mesothelioma, lymphangioendotheliosarcoma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, non-small cell lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia and heavy chain disease.

Cancers treated in accordance with preferred embodiments of the present invention include pancreatic cancer, colon cancer, lung cancer, prostate cancer, breast cancer, and brain metastases of these primary tumors and primary brain cancers such as gliomas.

The frequency of administration, dosage amounts, and the duration of treatment of each of the active agents may be adjusted depending on several factors including the overall health, size and weight of the patient and the severity of the particular cancer being treated. For example, duration of treatment with both actives may last for days, weeks, months, or until remission of the cancer is achieved. Due to the relative lack of toxicity of FTS and 2DG, it is not necessary to cycle the drugs, as is the case for cytotoxic cancer therapeutic drugs, e.g., chemotherapy. Relative timing of administration of each active agent is not critical.

Accordingly, FTS and 2DG may be administered sequentially, e.g., twice a day; or one drug on one day and one on another; each in separate dosage forms separated by a predetermined interval; or each may be administered in the same dosage form.

As used herein, the term "effective amount" refers to the dosages of FTS and 2DG that are effective for the treating, and thus include dosages that ameliorate symptom(s) of the cancer, diminish extent of disease, delay or slow disease progression, achieve partial or complete remission or prolong survival. The daily dose of FTS generally ranges from about 50 mg to about 1000 mg, and preferably about 200 mg to about 600 mg. The daily dose of 2DG generally ranges from about 500 mg to about 6 g, and preferably about 500 mg to about 2 g.

In some embodiments, both drugs are administered on a daily basis, e.g., each in single once-a-day or divided doses. They may be administered at the same or different times. In other embodiments, each drug is administered two or three times per day. In embodiments where the drugs are administered substantially simultaneously, they may be administered in the same dosage form.

Administration of FTS and 2DG may be cyclic. For example, in one treatment regimen, the Ras antagonist and 2DG are administered according to the following schedule: (1) administering Ras antagonist and 2DG daily for a period of three weeks followed by a one-week interval without actives ("off period"); and (2) repeating step (1) as many times as needed, e.g., until remission is achieved. Under this regimen, actives are administered in three-week cycles each separated by a one-week off period. In accordance with this regimen, a protocol may involve administering to a patient in need thereof both actives in different forms, (e.g., one as a capsule and the other a tablet) daily and substantially simultaneously, for a period of three weeks, followed by a one-week off period, and repeating as many times as needed, e.g., until remission is achieved.

In another embodiment, each active is administered sequentially and for a predetermined period. For example, a protocol may involve (1) administering to a patient in need thereof FTS daily (capsule form) for a period of three weeks, followed by (2) a one-week period of 2DG daily (tablet form), and repeating the sequence of steps 1 and 2 as many times as needed, e.g., until remission is achieved. Another protocol may involve (1) administration of FTS daily (capsule form) for a period of one week, followed by (2) a two-week period of 2DG plus Ras antagonist daily (tablet form), followed by (3) a one-week off period; and repeating the sequences of steps (1)-(3) as many times as needed, e.g., until remission is achieved.

The methods and compositions of the present invention may be used for the treatment of cancer in mammals, particularly humans. The actives may be administered in accordance with standard methods. In some embodiments, FTS and 2DG are both administered orally e.g., in the same dosage form. In oral dosage forms, the FTS is typically present in an amount of about 100 mg to about 500 mg, and preferably about 100 mg to about 300 mg. The 2DG is typically present in an amount of about 400 mg to about 4 g, and preferably about 400 mg to about 1g.

Compositions for use in the present invention (which contain either or both active pharmaceutical agents) can be prepared by bringing either or both active ingredients into association with (e.g., mixing with) a pharmaceutically acceptable carrier. Suitable carriers are selected based in part on the mode of administration. Carriers are generally solid or liquid. In some cases, compositions may contain solid and liquid carriers. Compositions suitable for oral administration that contain either or both actives are preferably in solid dosage forms such as tablets (e.g., including film-coated, sugar-coated, controlled or sustained release); capsules, e.g., hard gelatin capsules (including controlled or sustained release) and soft gelatin capsules, and powders or granules. The compositions, however, may be contained in other carriers that enable administration to a patient in other oral forms, e.g., a liquid or gel. In any such form, the composition is divided into individual or combined doses containing predetermined quantities of the active ingredients.

Oral doses may be prepared by mixing the active pharmaceutical ingredient or ingredients with one or more appropriate carriers (excipients), and then formulating the composition into the desired dosage form e.g., compressing the composition into a tablet or filling the composition into a capsule or a pouch. Typical excipients useful as bulking agents or diluents, binders, buffers or pH adjusting agents, disintegrants (including crosslinked and super disintegrants such as croscarmellose), glidants, and/or lubricants include lactose, starch, mannitol, microcrystalline cellulose, ethyl cellulose, sodium carboxymethyl cellulose, hydroxypropylmethyl cellulose, dibasic calcium phosphate, acacia, gelatin, stearic acid, magnesium stearate, corn oil, vegetable oils, and polyethylene glycols, and others known to the pharmaceutical practitioner. Coating agents such as sugar, shellac, and synthetic polymers may be employed. Dyes and other colorants and preservatives may be added as well. See, *Remington's Pharmaceutical Sciences*, The Science and Practice of Pharmacy, 20th Edition, (2000).

Liquid form compositions include, for example, solutions, suspensions, emulsions, syrups, elixirs and pressurized compositions. The active ingredient or ingredients, for example, can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmoregulators.

Suitable examples of liquid carriers for oral administration include water (particularly containing additives as above, e.g., cellulose derivatives, preferably in suspension in sodium carboxymethyl cellulose solution), alcohols (including monohydric alcohols (including monohydric alcohols and polyhydric alcohols, e.g., glycerin and non-toxic glycols) and their derivatives, and oils (e.g., fractionated coconut oil and arachis oil).

Carriers suitable for preparation of compositions for parenteral administration include Sterile Water for Injection, Bacteriostatic Water for Injection, Sodium Chloride Injection (0.45%, 0.9%), Dextrose Injection (2.5%, 5%, 10%), Lactated Ringer's Injection, and the like. Compositions containing 2DG are preferably essentially free of glucose or complex sugars that contain glucose. Dispersions can also be prepared in glycerol, liquid polyethylene glycols and mixtures thereof, and in oils. Compositions may also contain tonicity agents (e.g., sodium chloride and mannitol), antioxidants (e.g., sodium bisulfite, sodium metabisulfite and ascorbic acid) and preservatives (e.g., benzyl alcohol, methyl paraben, propyl paraben and combinations of methyl and propyl parabens).

For treatment of brain cancers, (e.g., gliomas and brain metastases of other primary tumors) FTS and 2DG can be administered by convection-enhanced delivery techniques, which as used herein, refers to any non-manual delivery of agents. In the context of the present invention, examples of convection-enhanced delivery (CED) of FTS and 2DG include infusion pumps and osmotic pumps. Osmotic and infusion pumps are commercially available from a variety of suppliers, e.g., Alzet Corporation, Hamilton Corporation, and Aiza, Inc.

Typically, delivery of FTS and 2DG is administered using a catheter, cannula or other injection device that is inserted into CNS tissue. One of skill in the art could readily determine which general area of the CNS is the most appropriate target. For example, stereotaxic maps and positioning devices are available, for example from ASI Instruments. Positioning may also be conducted by using anatomical maps obtained by CT and/or MRI imaging of the patient's brain to help guide the injection device to the chosen target. Additionally, one of ordinary skill in the art could readily determine the optimal dosing regimens that include the flow rate, infusion volume, and concentration of the infused agent.

The efficacy of the methods and compositions of the invention are demonstrated in various in vitro studies confirming the enhanced effects of farnesylthiosalicylic acid (FTS) and 2-deoxy-D-glucose (2DG).

Experimental Design

The purpose of these experiments was to determine whether the combination of FTS and 2DG can lead to enhanced tumor cell growth inhibition or death. The experiments were performed in vitro using human glioblastoma (GBM) cell lines U87 and U373, the pancreatic cell line Panc-1 and three primary pancreatic cancer cell lines designated pp78, pp109 and pp161. The results demonstrated that tumor cell growth inhibition in vitro is strongly enhanced by the combination of FTS and 2-DG. Specifically, results indicated that in pancreatic carcinoma cell line Panc-1, a combination of FTS and 2-deoxy-D-glucose (2DG) induced cell death under conditions where neither drug alone induced cell death. Similarly, in primary pancreatic tumor cell lines pp109, pp161, and pp 78, results indicated that a combined dosage of FTS and 2DG induced cell death under conditions where neither drug alone induced cell death. Finally, in glioblastoma cell lines (GBMs) U87 and U373, FTS and 2DG in combination also induced cell death under conditions where neither drug alone induced cell death.

Materials and Methods

All materials for cell culture and determination of cell growth and death were detailed in earlier publications. [Blum, R., Jacob-Hirsch, J., Amariglio, N., Rechavi, G. and Kloog, Y., Cancer Res 65:999-1006 (2005); Yaari, S., Jacob-Hirsch, J., Amariglio, N., Haklai, R., Rechavi, G. and Kloog, Y., Clin Cancer Res 11:4321-30 (2005)]. FTS was provided by Concordia Pharmaceuticals, Inc. 2DG was purchased from Sigma (cat #D3179). Cells were maintained in DMEM/10% FCS at a constant temperature of 37° C. in a humidified atmosphere of 95% air/5% $CO_2$. Cells were plated in 1 ml DMEM/5% FCS at a density of 10,000 in 24 wells plates, and treated 24 hours (h) later with 50 µM or 75 µM FTS or with the vehicle (0.1% $Me_2SO$). Forty-eight (48) h later the medium was replaced by a medium containing either 10 mM glucose or 5 mM glucose plus 5 mM 2DG. The FTS treated groups were replenished with the drug and the controls with 0.1% $Me_2SO$. Following incubation for 24 or 48 h, as specified in each experiment, the cells were stained with Hoechst 33258 (1 µg/mL) to determine the extent of cell death; the cells were incubated with the reagent for 5 min and stained nuclei were visualized by a fluorescence microscope. Additionally, phase contrast images were taken.

All experiments were performed and repeated at least four times. Data were collected by imaging each well then analyzed as follows: the total number of cells was calculated of the phase contrast images and the number of dead cells was calculated of the fluorescence images. The percentage of Hoechst stained dead cells ([dead cells/total number of cells]×100) was calculated and presented as means±SD.

FTS And 2DG in Pancreatic Carcinoma Cell Lines

EXAMPLE 1

FTS has been previously shown to inhibit anchorage-dependent and anchorage-independent growth of panc-1 and Mia Paca cells. [Kloog, Y. and Cox, A. D., Mol. Med. Today 6:398-402 (2000)]. FTS alone did not induce death of these carcinoma cells. The first set of experiments with 2DG was aimed at determining conditions in which 2DG had a minimal impact on cell survival. In this study, 2DG (5 mM) was combined with glucose (equimolar), which was previously shown to enhance cytotoxicity of topoisomerase inhibitors. [Dwarakanath, B. S., Khaitan, D. and Ravindranath, T., Cancer Biol. Ther. 3:864-70 (2004)]. Here, it was shown that 2DG alone did not affect cell survival. Namely, cell death was similar to that observed in controls (3%). Earlier reports showed that increasing the ratio of 2DG/glucose resulted in death of tumor cells. [Maher, J. C., Krishan, A. and Lampidis, T. J. Cancer Chemother Pharmacol 53:116-22 (2004)].

Figure 1A:
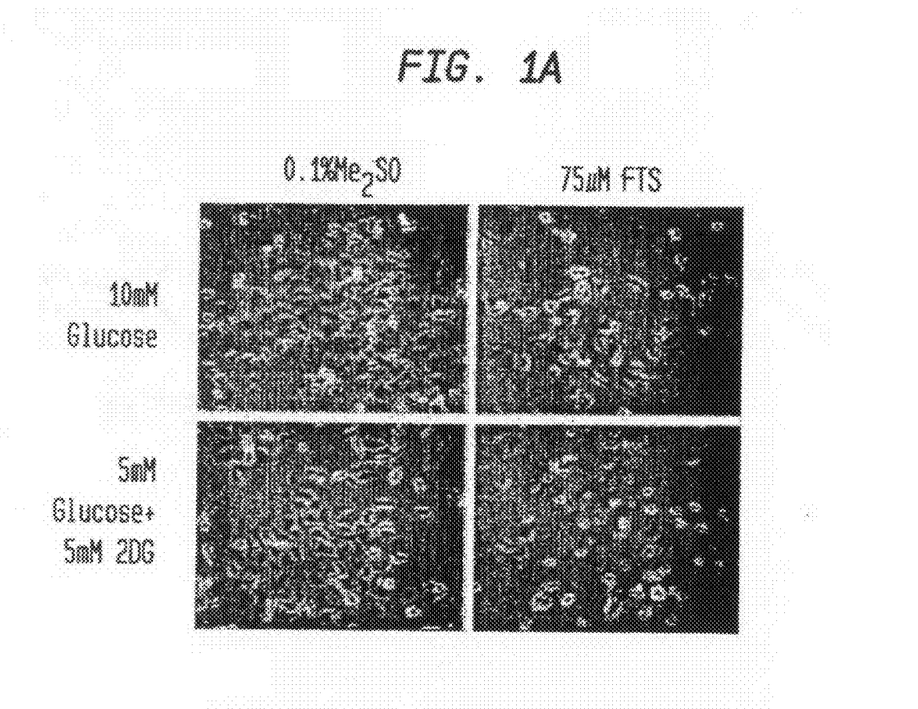
FIG. 1A depicts phase contrast images of cells treated with 10 mM glucose and 0.1% $Me_2SO$; 10 mM glucose and 75 µM FTS; 5 mM glucose plus 5 mM 2DG and 0.1% $Me_2SO$; and 5 mM glucose with 5 mM 2DG and 75 µM FTS in the pancreatic carcinoma cell line panc-1.
Figure 1B:
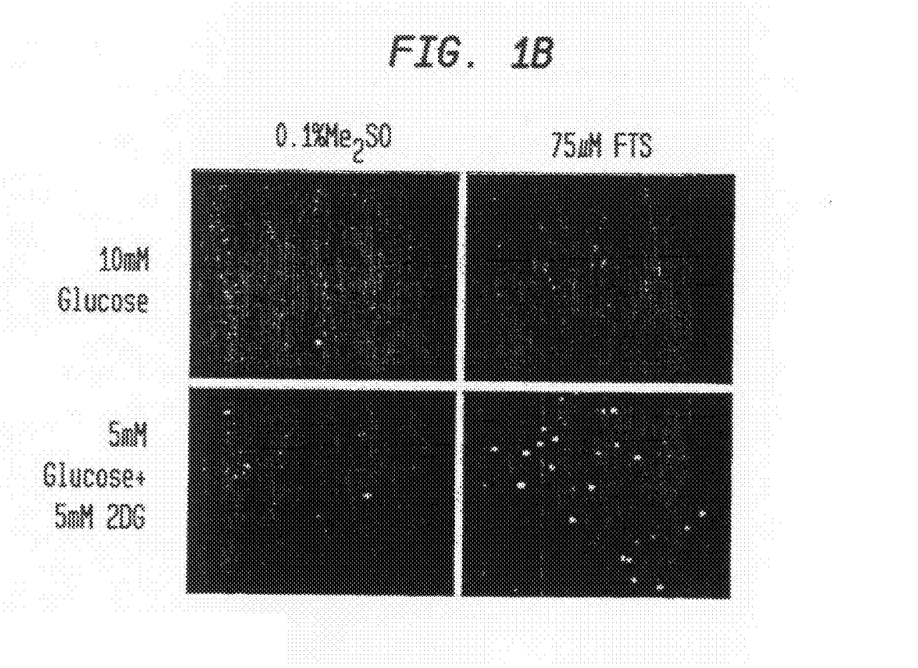
FIG. 1B depicts fluorescence images of the Hoechst stained cells treated with 10 mM glucose and 0.1% $Me_2SO$; 10 mM glucose and 75 µM FTS; 5 mM glucose plus 5 mM 2DG and 0.1% $Me_2SO$; and 5 mM glucose with 5 mM 2DG and 75 µM FTS in the pancreatic carcinoma cell line panc-1.
Figure 2:
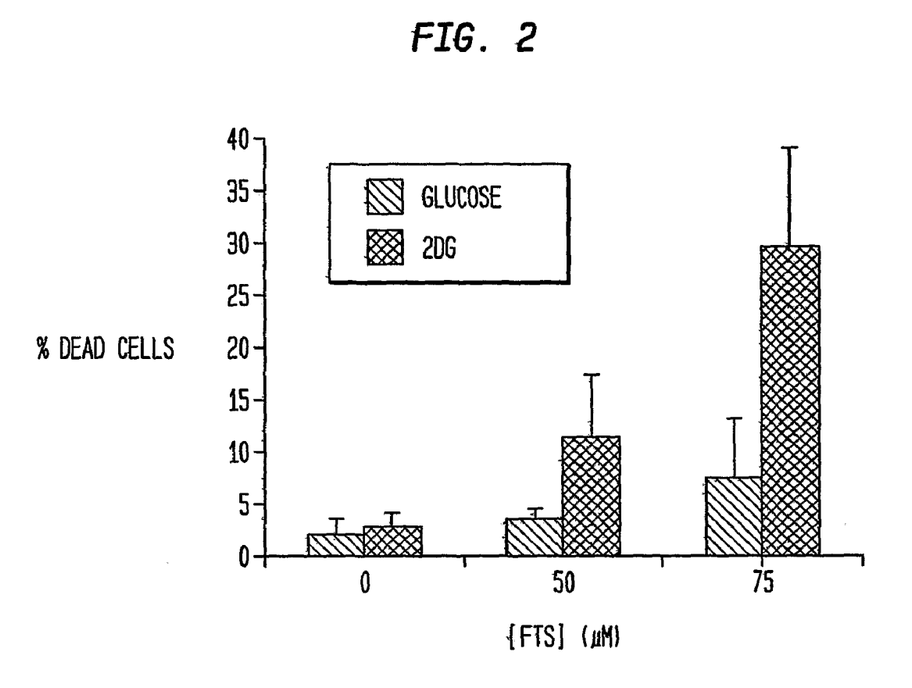
FIG. 2 is a bar graph showing the percentage of dead cells in pancreatic tumor cell line panc-1 following treatment of FTS and 2DG in combination, where concentration of FTS is administered at concentrations of 0 µM, 50 µM and 75 µM.
Figure 3A:
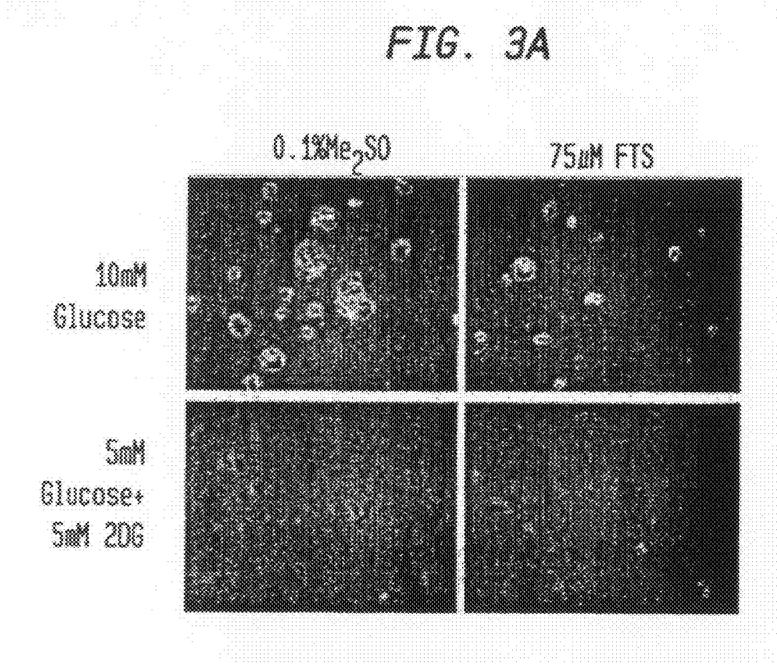
FIG. 3A depicts phase contrast images of cells treated with 10 mM glucose and 0.1% $Me_2SO$; 10 mM glucose and 75 µM FTS; 5 mM glucose plus 5 mM 2DG and 0.1% $Me_2SO$; and 5 mM glucose with 5 mM 2DG and 75 µM FTS in the primary pancreatic tumor cell line pp109.
Figure 3B:
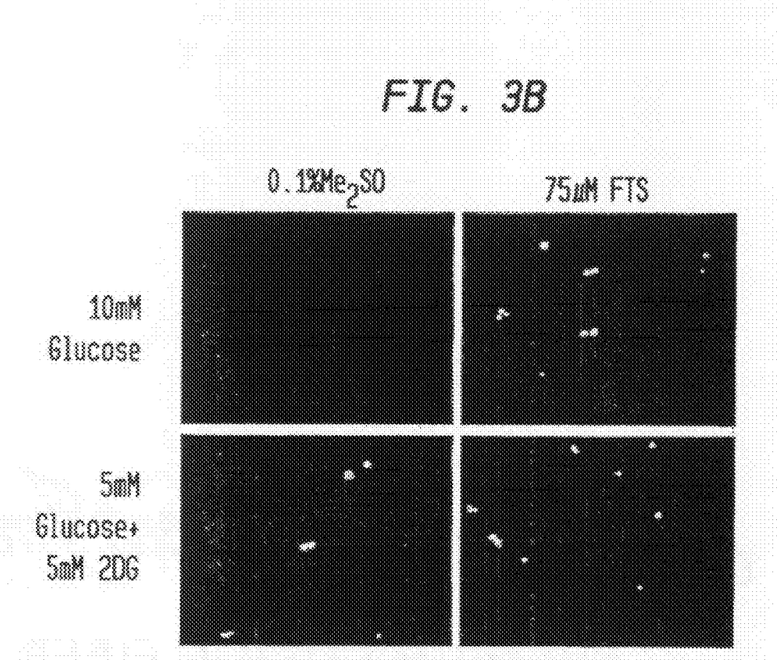
FIG. 3B depicts fluorescence images of the Hoechst stained cells treated with 10 mM glucose and 0.1% $Me_2SO$; 10 mM glucose and 75 µM FTS; 5 mM glucose plus 5 mM 2DG and 0.1% $Me_2SO$; and 5 mM glucose with 5 mM 2DG and 75 µM FTS in the primary pancreatic tumor cell line pp109.

Next, a four-armed experiment was performed that included vehicle control, 2DG, FTS and FTS plus 2DG-treated cells as detailed under Materials and Methods. Images collected of a typical experiment performed with panc-1 cells are shown in FIGS. 1A and 1B. The phase contrast images showed that 75 µM FTS alone induced as expected a decrease in cell number (about a 2-fold decrease). Similar results were obtained with 50 µM FTS alone (not shown). Treatment with 2DG alone also resulted in a decrease in cell number, but to a lower extent (FIG. 1A). Hoechst staining showed that each of these single-drug treatments did not cause a significant increase in cell death above the levels observed in the controls (FIG. 1B). Namely, the percentage of dead cells was 2, 3, 4, and 7, respectively, in control; 2DG; 50 µM FTS and 75 µM FTS treated cells. On the other hand, the combined treatment of 2DG and FTS caused a significant increase in cell death. Namely, the percentage of dead cells was 12 and 30, respectively, in 2DG plus 50 µM FTS and 2DG plus 75 µM FTS treated cells (FIG. 2). Thus, under conditions at which neither 2DG nor FTS alone induced death of panc-1 cells, the combination of the two active agents did induce cell death. This demonstrated the enhanced effect of the two actives in combination.

EXAMPLE 2

Figure 4:
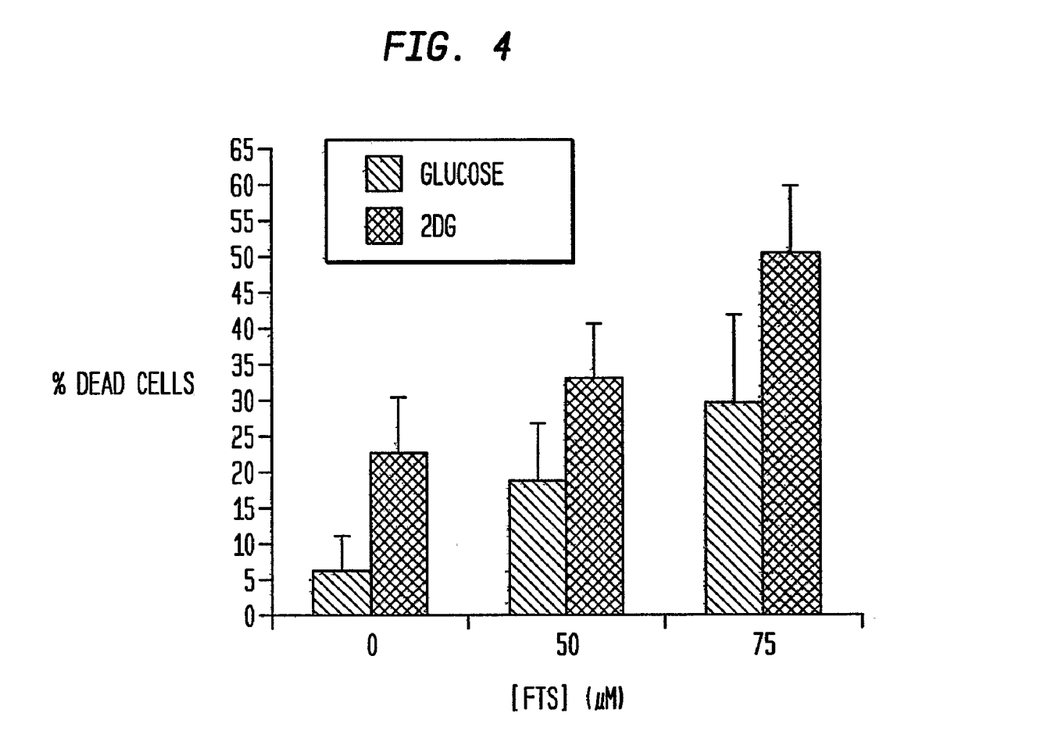
FIG. 4 is a bar graph showing the percentage of dead cells in primary pancreatic tumor cell line pp109 following treatment of FTS and 2DG in combination, where the concentration of FTS is administered at 0 µM, 50 µM and 75 µM.
Figure 5A:
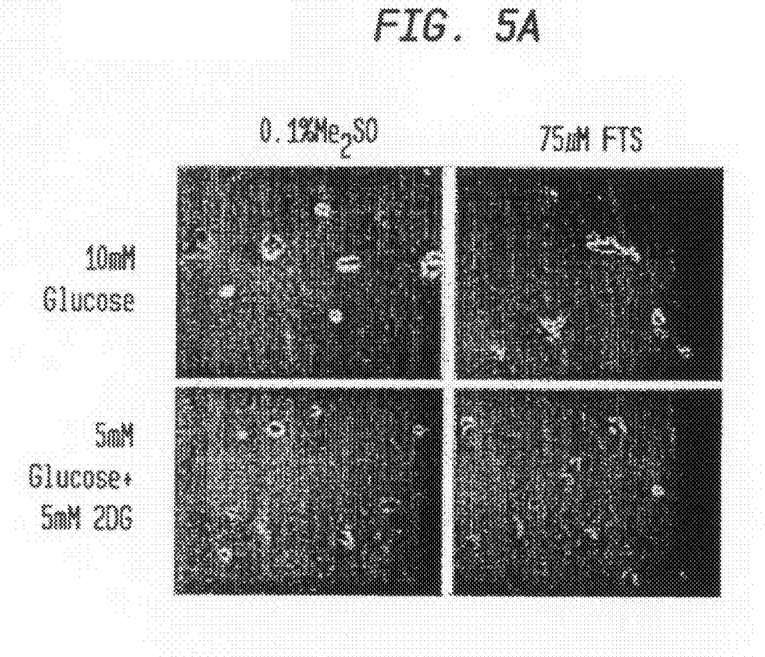
FIG. 5A depicts phase contrast images of cells treated with 10 mM glucose and 0.1% $Me_2SO$; 10 mM glucose and 75 µM FTS; 5 mM glucose plus 5 mM 2DG and 0.1% $Me_2SO$; and 5 mM glucose with 5 mM 2DG and 75 µM FTS in the primary pancreatic tumor cell line pp161.
Figure 5B:
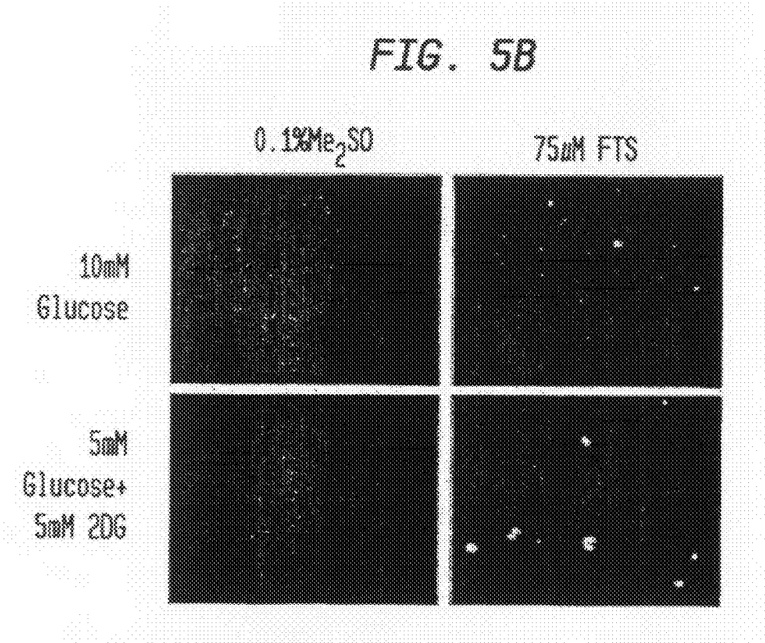
FIG. 5B depicts phase contrast images of cells treated with 10 mM glucose and 0.1% $Me_2SO$; 10 mM glucose and 75 µM FTS; 5 mM glucose plus 5 mM 2DG and 0.1% $Me_2SO$; and 5 mM glucose with 5 mM 2DG and 75 µM FTS in the primary pancreatic tumor cell line pp161.
Figure 6:
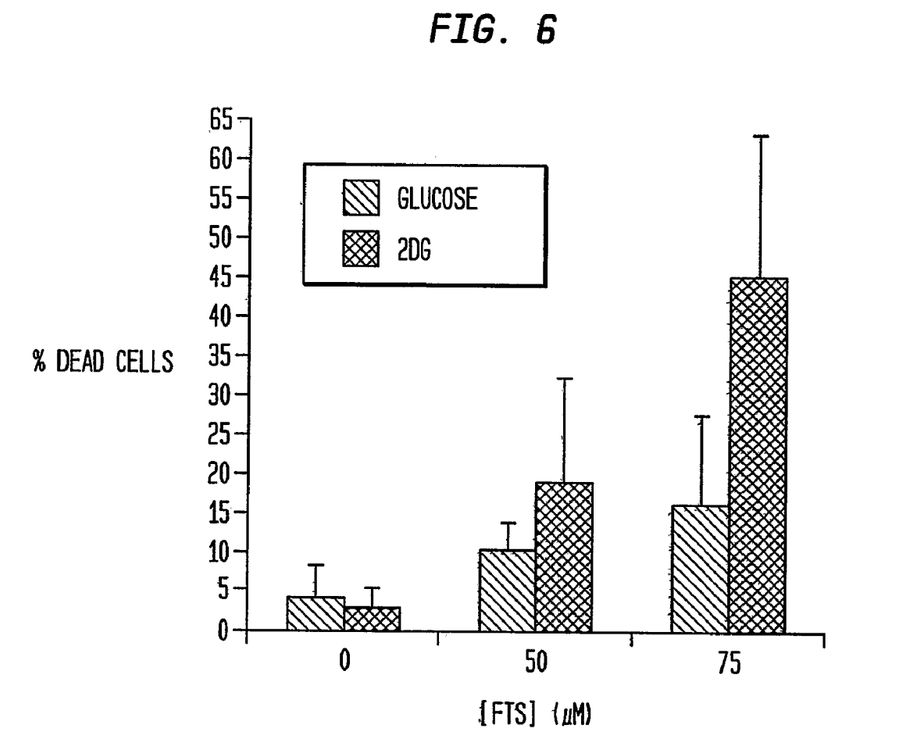
FIG. 6 is a bar graph showing the percentage of dead cells in the primary pancreatic tumor cell line pp161 following treatment of FTS and 2DG in combination, where FTS is administered at concentrations of 0 µM, 50 µM and 75 µM.
Figure 7A:
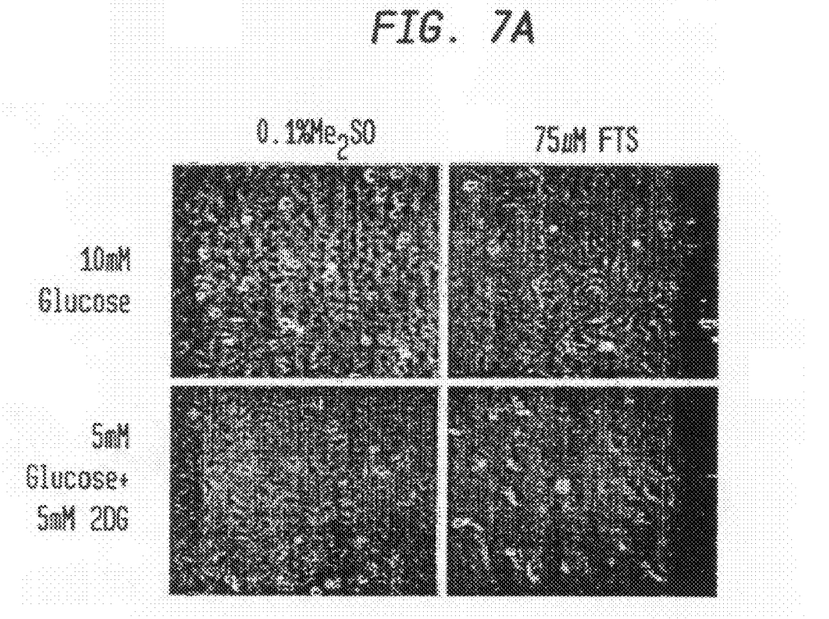
FIG. 7A depicts phase contrast images of cells treated with 10 mM glucose and 0.1% $Me_2SO$; 10 mM glucose and 75 µM FTS; 5 mM glucose plus 5 mM 2DG and 0.1% $Me_2SO$; and 5 mM glucose with 5 mM 2DG and 75 µM FTS in the primary pancreatic tumor cell line pp 78.
Figure 7B:
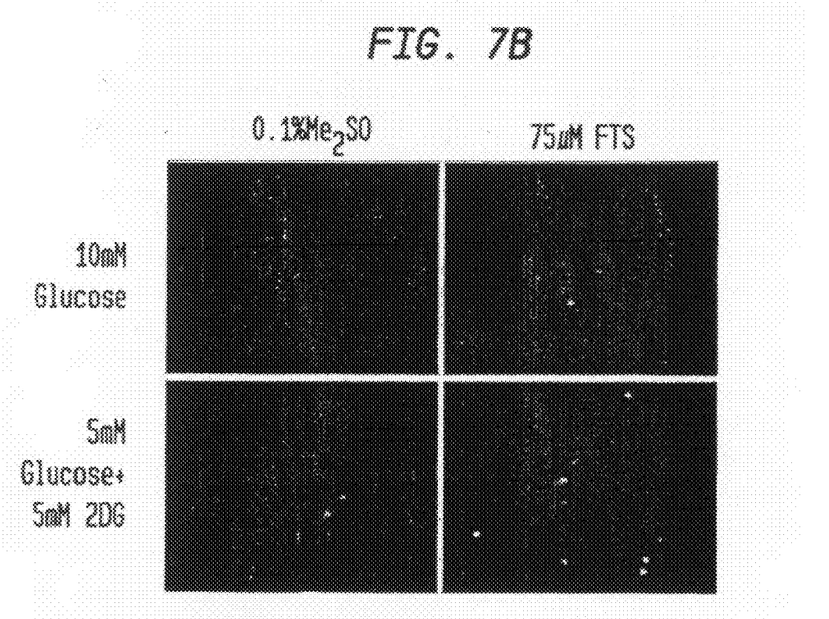
FIG. 7B depicts phase contrast images of cells treated with 10 mM glucose and 0.1% $Me_2SO$; 10 mM glucose and 75 µM FTS; 5 mM glucose plus 5 mM 2DG and 0.1% $Me_2SO$; and 5 mM glucose with 5 mM 2DG and 75 µM FTS in the primary pancreatic tumor cell line pp78.
Figure 8:
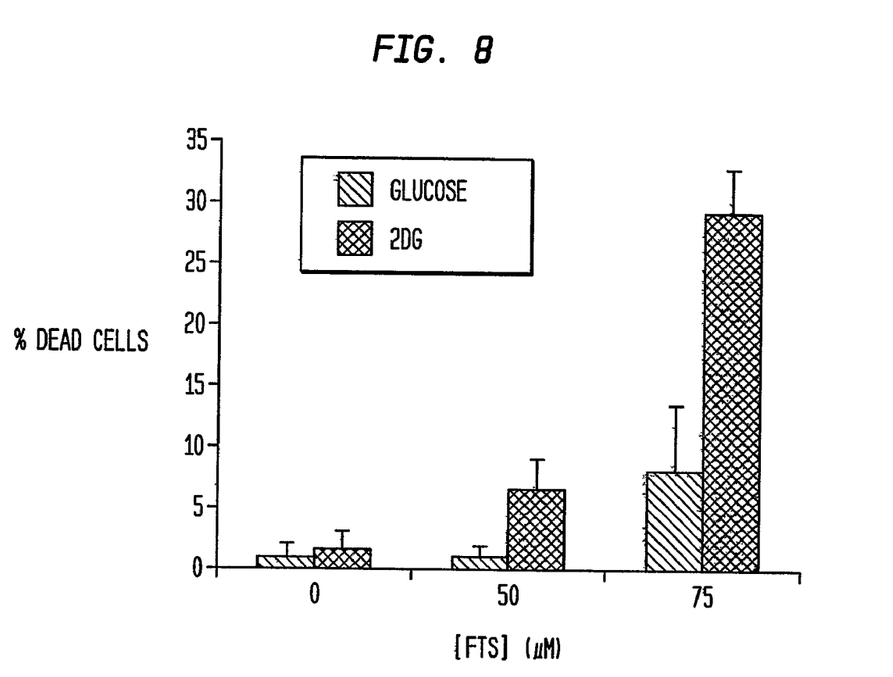
FIG. 8 is a bar graph showing the percentage of dead cells in primary pancreatic tumor cell line pp 78 following treatment of FTS and 2DG in combination, where FTS is administered at concentrations of 0 µM, 50 µM and 75 µM.

Here, a similar set of experiments with the primary pancreatic tumor cell lines pp109, pp161 and pp 78 was performed (FIGS. 3-8). The phase contrast images showed that 75 µM FTS alone induced a decrease (about a 2-fold decrease) in the total number of pp109, pp161 and pp 78 cells (FIGS. 3A, 5A and 7A). Treatment with 2DG alone also resulted in a decrease in cell number, but to a lower extent (FIGS. 3A, 5A and 7A). Hoechst staining showed that each of these single-drug treatments did not cause a significant increase in death of pp 78 and of pp161 cells above the levels observed in the controls, i.e., (FIGS. 5B and 7B) but induced death of pp109 cells (FIG. 3B). The combined treatment of 2DG and FTS caused a significant increase in cell death in all of the three cell lines (FIGS. 4, 6 and 8). In pp109 cell lines, the combined treatment resulted in an effect that was additive, and in pp 78 and pp161 cells, the combined treatment resulted in a greater than additive effect. Thus, the beneficial impact of FTS and 2DG treatment observed in panc-1 cells was also apparent in the primary pancreatic tumor cell lines.

FTS and 2DG in Human GBM Cell Lines

Human glioblastoma cells (GBMs) present a case that is different from that of panc-1 cells with respect to the impact of the Ras inhibitor FTS. This occurs because, unlike its effect in panc-1 cells, in GBM cells, FTS has been reported to induce both growth arrest and cell death. [Blum, R., Jacob-Hirsch, J., Amariglio, N., Rechavi, G. and Kloog, Y., Cancer Res 65:999-1006 (2005); Yaari, S., Jacob-Hirsch, J., Amariglio, N., Haklai, R., Rechavi, G. and Kloog, Y., Clin Cancer Res 11:4321-30 (2005)]. Therefore, it was examined whether the combined treatment with 2DG could enhance the cell death induced by FTS alone using conditions similar to those described above with the pancreatic carcinoma cell lines. Namely, four-armed experiments were performed where the GBM cell lines U87 and U373 were treated with vehicle, FTS, alone, 2DG alone or FTS plus 2DG. Here, it was shown that in glioblastoma cell lines U87 and U373, FTS and 2DG in combination also induced cell death under conditions where neither drug alone induced cell death.

EXAMPLE 3

Figure 9A:
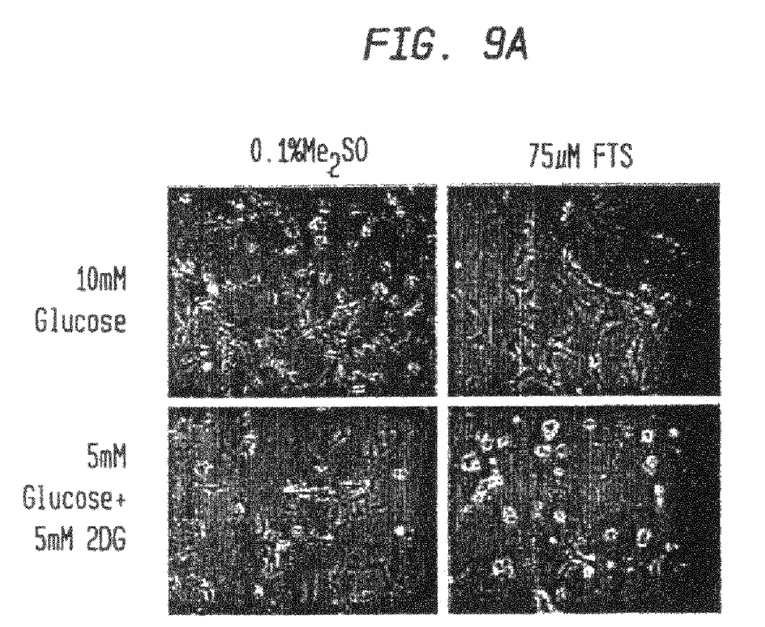
FIG. 9A depicts phase contrast images of cells treated with 10 mM glucose and 0.1% $Me_2SO$; 10 mM glucose and 75 µM FTS; 5 mM glucose plus 5 mM 2DG and 0.1% $Me_2SO$; and 5 mM glucose with 5 mM 2DG and 75 µM FTS in the human glioblastoma cell line U87.
Figure 9B:
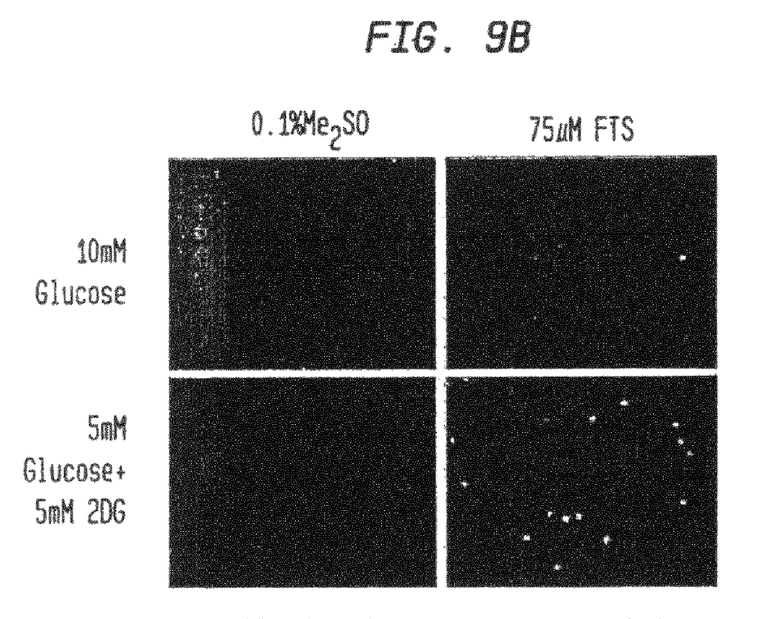
FIG. 9B depicts phase contrast images of cells treated with 10 mM glucose and 0.1% $Me_2SO$; 10 mM glucose and 75 µM FTS; 5 mM glucose plus 5 mM 2DG and 0.1% $Me_2SO$; and 5 mM glucose with 5 mM 2DG and 75 µM FTS in the human glioblastoma cell line U87.
Figure 10:
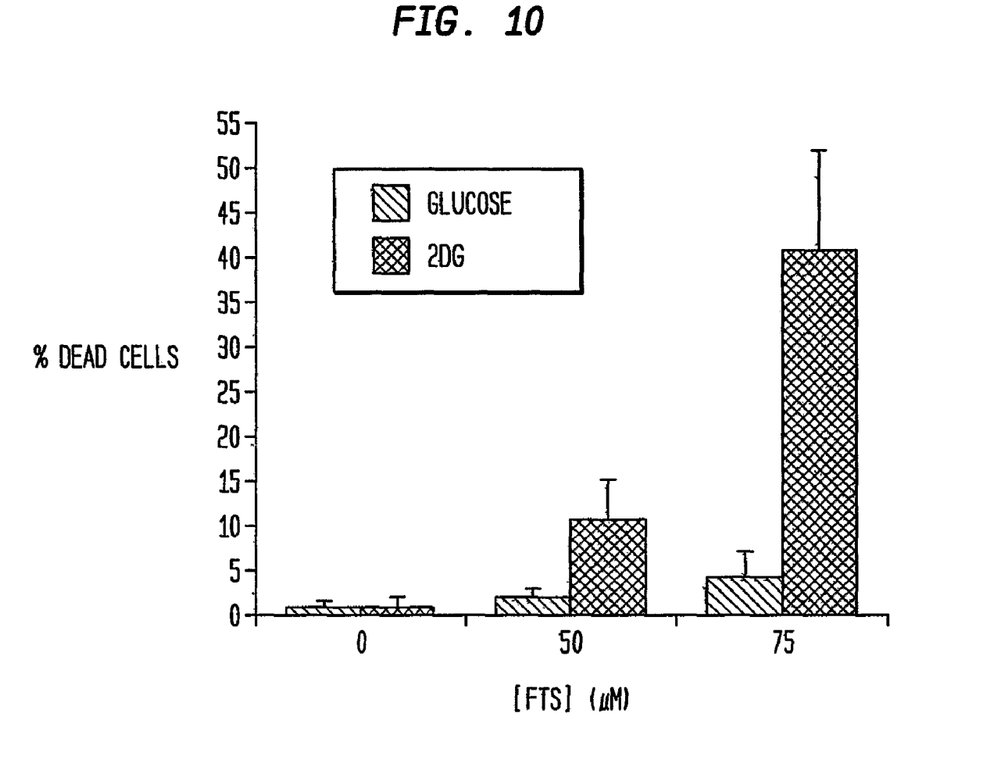
FIG. 10 is a bar graph showing the percentage of dead cells in human glioblastoma cell line U87 following treatment of FTS and 2DG in combination, where FTS is administered at concentrations of 0 µM, 50 µM and 75 µM.
Figure 11A:
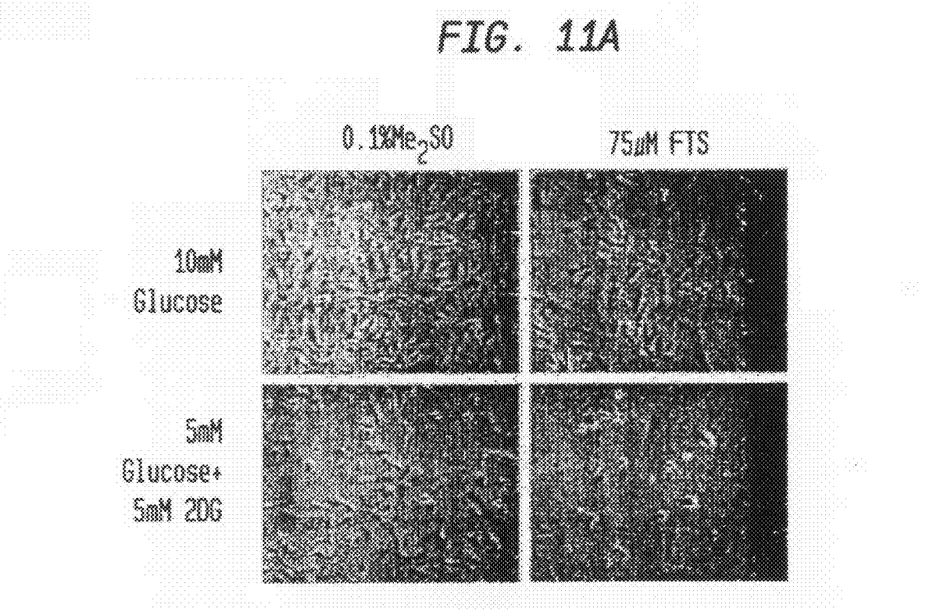
FIG. 11A depicts phase contrast images of cells treated with 10 mM glucose and 0.1% $Me_2SO$; 10 mM glucose and 75 µM FTS; 5 mM glucose plus 5 mM 2DG and 0.1% $Me_2SO$; and 5 mM glucose with 5 mM 2DG and 75 µM FTS in the human glioblastoma cell line U373.
Figure 11B:
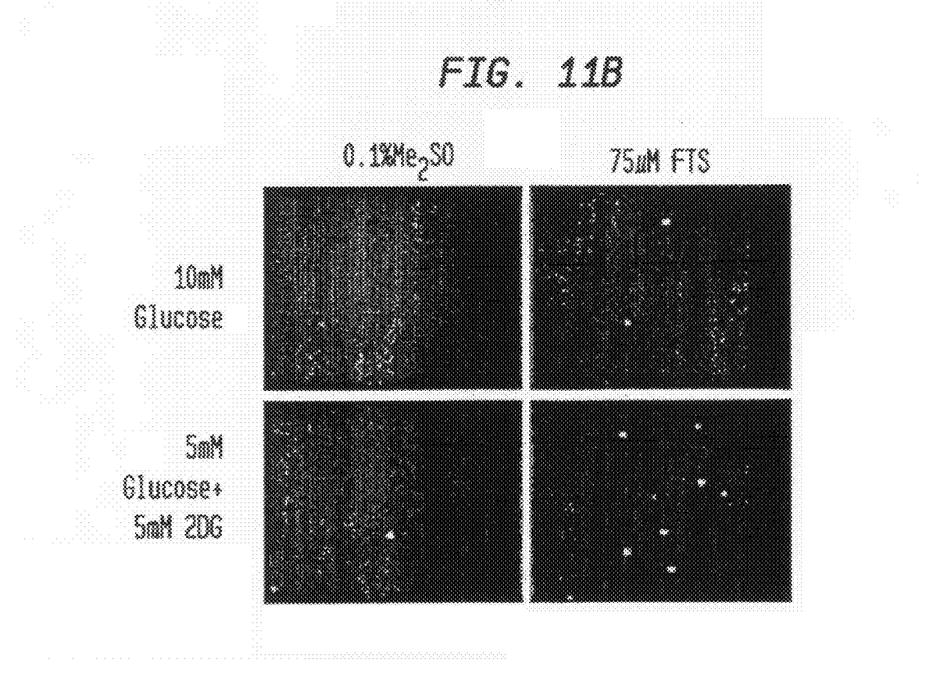
FIG. 11B depicts phase contrast images of cells treated with 10 mM glucose and 0.1% $Me_2SO$; 10 mM glucose and 75 µM FTS; 5 mM glucose plus 5 mM 2DG and 0.1% $Me_2SO$; and 5 mM glucose with 5 mM 2DG and 75 µM FTS in the human glioblastoma cell line U373.
Figure 12:
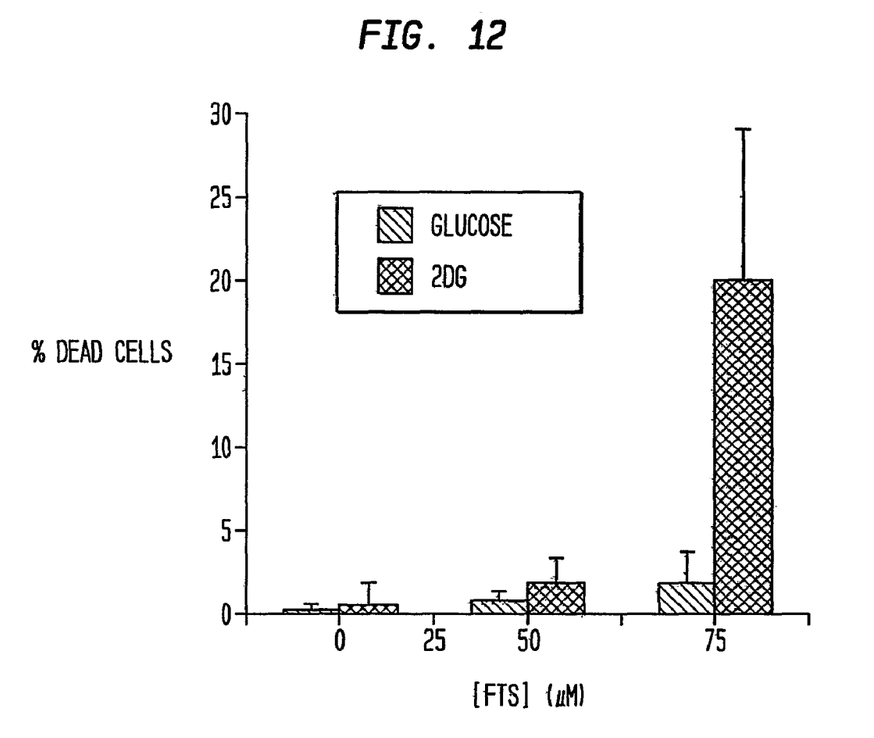
FIG. 12 is a bar graph showing the percentage of dead cells in human glioblastoma cell line U373 following treatment of FTS and 2DG in combination, where FTS is administered at concentrations of 0 μM, 50 μM and 75 μM.

The phase contrast images in FIGS. 9A (U87 cells) and 11A (U373 cells) showed that FTS or 2DG alone induced a decrease in total cell number and that the combined treatment enhanced this effect. Hoechst staining confirmed that the single treatment alone caused no significant increase in cell death. The combined treatment, however, induced a marked increase in cell death (FIGS. 9B for U87 cells and 11B for U373 cells). Statistical analyses of these results are shown in FIGS. 10 and 12, respectively, for U87 and U373 cells. Taken together, these results show that the combined treatments of FTS and 2DG enhanced the induction of GBM cell death.

Representative Formulations of Oral Dosage Forms

EXAMPLE 4

Capsules of FTS (100 mg) and 2DG (400 mg)

FTS active pharmaceutical ingredient (1000 g), 2DG active pharmaceutical ingredient (4000 g), microcrystalline cellulose (1000 g), and magnesium stearate (50 g) are blended to uniformity and filled into hard gelatin capsules. Assuming a 5% loss on material transfers and encapsulating machine start-up, adjustment, and shut-down, approximately 9,500 FTS 100 mg/2DG 400 mg capsules are yielded.

By adjusting fill weight, capsule size, or the relative amount of the two actives, other hard capsule strengths are prepared.

EXAMPLE 5

Tablets of FTS (200 mg) and 2DG (400 mg)

FTS active pharmaceutical ingredient (2000 g), 2DG active pharmaceutical ingredient (4000 g), microcrystalline cellulose (1000 g), croscarmellose sodium (200 g), magnesium stearate (35 g), and colloidal silicon dioxide (15 g) are blended to uniformity and compressed into tablets weighing 725 mg. Assuming a 5% loss on material transfers and tablet press start-up, adjustment, and shut-down, approximately 9500 FTS 200 mg/2DG 400 mg tablets are yielded.

By adjusting tablet weight or the relative amounts of the two actives, other tablet strengths are prepared.

EXAMPLE 6

Soft Gelatin Capsules of FTS (100 mg) and 2DG (100 mg)

A mixture of FTS active pharmaceutical ingredient (500 g) and 2DG active pharmaceutical ingredient (500 g) is uniformly dispersed in a mixture of corn oil (3000 g), lecithin (30 g), and Tween-80 (120 g) and filled into soft gelatin capsules. Assuming a 5% loss on material transfers and soft gelatin encapsulating machine start-up, adjustment, and shut-down, approximately 4750 FTS 100 mg/2DG 100 mg soft gelatin capsules are yielded.

By adjusting fill weight or the relative amounts of the two actives, other soft gelatin capsule strengths are prepared.

EXAMPLE 7

Pouches Containing FTS (250 mg) and 2DG (1.0 g)

FTS active pharmaceutical ingredient (2.5 kg), 2DG active pharmaceutical ingredient (10.0 kg), microcrystalline cellulose (2.0 kg), and methylparaben (10 g) are blended to uniformity and filled into individual pouches each containing approximately 1.45 g. Assuming a 5% loss on material transfers, and pouch-filling machine start-up, adjustment, and shut-down, approximately 9,500 pouches containing FTS 250 mg/2DG 1.0 g are yielded.

The publications cited in the specification, patent publications and non-patent publications, are indicative of the level of skill of those skilled in the art to which this invention pertains. All these publications are herein incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A pharmaceutical composition useful in the treatment of pancreatic cancer or a glioblastoma, comprising effective amounts of a Ras antagonist represented by the formula:

wherein
$R^1$ represents farnesyl or geranylgeranyl;
$R^2$ is $COOR^7$, or $CONR^7R^8$, wherein $R^7$ and $R^8$ are each independently hydrogen, alkyl or alkenyl;
$R^3$, $R^4$, $R^5$ and $R^6$ are each independently hydrogen, alkyl, alkenyl, alkoxy, halo, trifluoromethyl, trifluoromethoxy, or alkylmercapto; and
X represents S; or a pharmaceutically acceptable salt thereof; and
2-deoxyglucose (2DG); and
a pharmaceutically acceptable carrier.

2. The composition of claim 1, wherein said Ras antagonist is farnesylthiosalicylic acid (FTS).

3. The composition of claim 1, wherein said Ras antagonist is S-geranylgeranyl-thiosalicylic acid (GGTS).

4. The composition of claim 1, wherein said Ras antagonist is present in an amount of about 100 mg to about 500 mg.

5. The composition of claim 1, wherein said 2DG is present in an amount of about 400 mg to about 1000 mg.

6. The composition of claim 1, which is in the form of a tablet.

7. The composition of claim 1, which is in the form of a capsule.

8. A method of treating pancreatic cancer or a glioblastoma, comprising administering to a human in need thereof effective amounts of a Ras antagonist represented by the formula:

wherein
$R^1$ represents farnesyl or geranylgeranyl;
$R^2$ is $COOR^7$, or $CONR^7R^8$, wherein $R^7$ and $R^8$ are each independently hydrogen, alkyl or alkenyl;
$R^3$, $R^4$, $R^5$ and $R^6$ are each independently hydrogen, alkyl, alkenyl, alkoxy, halo, trifluoromethyl, trifluoromethoxy, or alkylmercapto; and
X represents S; or a pharmaceutically acceptable salt thereof; and
2-deoxyglucose (2DG).

9. The method of claim 8, wherein the Ras antagonist is FTS.

10. The method of claim 8, wherein the Ras antagonist is GGTS.

11. The method of claim 8, wherein the effective amount of the Ras antagonist is about 50 mg to about 1000 mg.

12. The method of claim 8, wherein the effective amount of the 2DG is about 500 mg to about 6000 mg.

13. The method of claim 8, wherein the treatment comprises separate administration of the Ras antagonist and the 2DG.

14. The method of claim 8, wherein the treatment comprises oral administration of the Ras antagonist and 2DG in the same oral dosage form.

15. The method of claim 8, wherein the treatment comprises oral administration of the Ras antagonist and parenteral administration of 2DG.

16. The method of claim 8, wherein the treatment comprises convection-enhanced delivery of the Ras antagonist and 2DG.

17. The method of claim 8, wherein the cancer is pancreatic cancer.

18. The method of claim 8, wherein the cancer is a glioblastoma.

* * * * *